United States Patent [19]
Hocherman

[11] Patent Number: 5,772,611
[45] Date of Patent: Jun. 30, 1998

[54] SYSTEM AND METHOD FOR DETECTION AND QUANTIFICATION OF PARKINSON'S DISEASE

[76] Inventor: Shraga Hocherman, 9 Ruth St., Haifa, Israel

[21] Appl. No.: 594,303

[22] Filed: Jan. 30, 1996

Related U.S. Application Data

[63] Continuation-in-part of Ser. No. 366,300, Dec. 29, 1994, abandoned.

[51] Int. Cl.[6] .................................................. A61B 5/103
[52] U.S. Cl. ............................................................ 600/595
[58] Field of Search ..................................... 128/774, 782

[56] References Cited

U.S. PATENT DOCUMENTS

| | | |
|---|---|---|
| 4,760,851 | 8/1988 | Fraser et al. . |
| 4,885,687 | 12/1989 | Carey . |
| 4,889,422 | 12/1989 | Pavlidis . |
| 4,922,925 | 5/1990 | Crandall et al. . |

OTHER PUBLICATIONS

"Quantification of tremor with a digitizing tablet", Roger J. Elble et al., *Journal of Neuroscience Methods*, vol. 32 (1990) pp. 193–198.

*Primary Examiner*—Max Hindenburg
*Assistant Examiner*—Pamela L. Wingood
*Attorney, Agent, or Firm*—Pollock, Vande Sande & Priddy

[57] ABSTRACT

The invention provides a system for detection and quantification of Parkinson's disease, including a substantially planar digitizer tablet fixedly mounted on a base plate and capable of translating graphic information into digital information displayable, via a computer, as graphic information on a monitor screen viewable by the subject to be tested, and a handle to be gripped and steered by the subject. The handle is fixedly attached to, and supported by, a guide providing the handle with two degrees of freedom in translation in a plane above, and substantially parallel to, the plane of the digitizer tablet. The system further includes a stylus moving together with the handle and adapted to produce signals sensible by the digitizer tablet, and means to produce on the monitor screen a model path of a predetermined shape and size, as well as a target to be tracked by the subject, the target moving at a predetermined speed along the model path. A method for detection and quantification of Parkinson's disease is also described and claimed.

10 Claims, 2 Drawing Sheets

SYSTEM AND METHOD FOR DETECTION AND QUANTIFICATION OF PARKINSON'S DISEASE

The present application is a CIP of U.S. patent application Ser. No. 08/366,300, filed Dec. 29, 1994 now abandoned.

FIELD OF INVENTION

The present invention relates to a system and method for detection and quantification of Parkinson's disease.

BACKGROUND OF INVENTION

The impairment of voluntary movement in Parkinson's disease (hereinafter, "PD") may be characterized by increased movement latency, slowing of movement execution, rigidity, tremor, and difficulties in execution of multi-component movements, which together result in reduced coordination and fluidity of movement. These motor control problems may be attributed to various causes, including a delay in proprioceptive feedback or inability to use such feedback for control of movement; faulty transmission of motor commands from the "decision-making" system to the effector mechanisms; loss of the ability to generate ramp movements; inability to generate preprogrammed (ballistic) movements, with consequent reliance on concurrent sensory information, a deficit in the automatic execution of learned motor plans that consist of movement sequences; and inability to regulate EMG activity over time in accordance with movement requirements. Thus, the motor deficits in PD may reflect abnormal sensory processing as well as impairments at several levels of the motor control hierarchy.

Many of the above motor control problems are revealed during performance of reaching movements, which involve feed-forward (open loop) as well as feed-back (closed loop) modes of control. The feed-forward mode is disrupted in PD patients, who are unable to perform rapid, accurate pointing movements under open loop (no vision of hand) conditions. This impairment in feed-forward control applies not only to fast reaching, but also to slow manuovisual tracking, as revealed by the fact that abolishment of visual feedback during performance of a well-rehearsed visuomanual tracking task causes PD patients to lose track of the target. This reduced capacity to execute feed-forward control contrasts with the seemingly unimpaired ability to utilize visual feedback, which in turn enables PD patients to maintain normal tracking capability when predictive planning is of no value, i.e., along unpredictable paths. Thus, PD leads to increased reliance on corrective visual feedback, which limits the movement's speed and determines its final accuracy.

It should, however, be noted that a mere quantification of tremor, a prominent symptom of PD, such as has been attempted in the past, using, e.g., a digitizer tablet to turn hand movements into digital information, does not clearly provide unambiguous results, as the amplitude of tremors does not correlate with the presence, severity and progress of PD.

It is therefore one of the objects of the present invention to provide a system and a method that, by facilitating the objective measurement and evaluation of the above phenomena and dependencies, would assist in the diagnosis of PD and in an objective determination of the stage and course of this disease.

It is a further object of the system and method according to the invention to elicit criteria that will help the clinician to distinguish between the frequently similar symptoms produced by the common debilities and infirmities of old age, and those characteristic of PD.

According to the invention, the above objectives are achieved by providing a system for detection and quantification of Parkinson's disease, comprising a substantially planar digitizer tablet fixedly mounted on a base plate and capable of translating graphic information into digital information displayable, via computer means, as graphic information on a monitor screen viewable by the subject to be tested; a handle to be gripped and steered by said subject, said handle being fixedly attached to, and supported by, guide means providing said handle with two degrees of freedom in translation in a plane above, and substantially parallel to, the plane of said digitizer tablet; a stylus moving together with said handle and adapted to produce signals sensible by said digitizer tablet, and means to produce on said monitor screen a model path of a predetermined shape and size, as well as a target to be tracked by said subject, said target moving at a predetermined speed along said model path.

The invention further provides a method for detection and quantification of Parkinson's disease, comprising the steps of providing a substantially planar digitizer tablet fixedly mounted on a base plate and capable of translating graphic information into digital information displayable, via computer means, as graphic information on a monitor screen viewable by the subject to be tested; a handle to be gripped and steered by said subject, said handle being fixedly attached to, and supported by, guide means providing said handle with two degrees of freedom in translation in a plane above, and substantially parallel to, the plane of said digitizer tablet; a stylus moving together with said handle and adapted to produce signals sensible by said digitizer tablet, and means to produce on said monitor screen a model path of a predetermined shape and size, as well as a target moving at a predetermined speed along said model path; having the subject grip said handle and track a target displayed on said monitor screen, which target moves at a controlled speed along a visible path; having the subject grip said handle and trace a model path displayed on said monitor in said subject's own time; determining the number of times said moving target was lost during the tracking thereof; determining the mean vectorial error occurring during the tracing of said model path; determining the cumulative movement time with a vectorial error of a preset magnitude, and comparing the results of said determinations with a set of available values, to determine the likelihood of said subject to suffer from Parkinson's disease.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a perspective view of the device according to the invention;

FIG. 2 represents the graphic results of a test with a control subject, and

FIG. 3 represents the graphic results of a test with a PD patient.

DETAILED DESCRIPTION OF THE INVENTION

Figure 1:
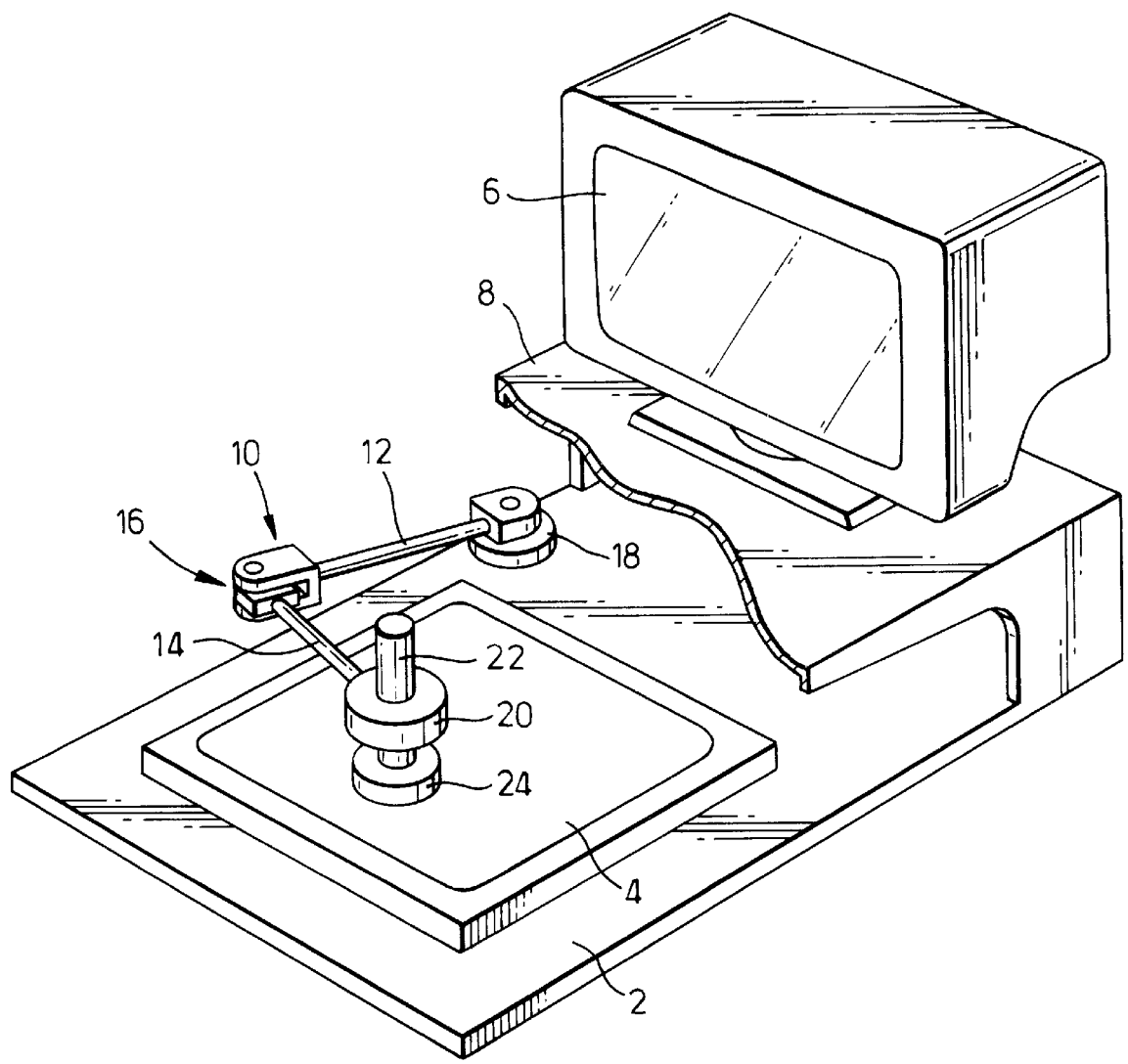

Referring now to the drawings, there is seen in FIG. 1 a base plate 2 on which is mounted a digitizer tablet 4. This planar tablet (e.g., Gridmaster™, Numonics) is a device capable, in conjunction with a stylus (not shown) of translating graphic information into digital information displayable, via a computer (not shown) on a monitor screen 6 mounted on a top plate 8. The space between base plate 2 and top plate 8 is freely accessible from either side.

Between base plate 2 and top plate 8 there is seen a mechanical linkage 10 consisting of two bars 12, 14 articulated to one another by a hinge joint 16. The free end of bar 12 is pivotably mounted on a plate 18 fixedly attached to base plate 2, while to the free end of bar 14 there is attached an annular member 20 which grips a handle 22 accommodating the above-mentioned stylus in its easily sliding base 24, made, e.g., of Teflon®. Base 24 is disposed in close proximity to, but does not touch, tablet 4. Linkage 10 provides handle 22, gripped and guided by the subject's hand, with two degrees of freedom in translation in a plane above, and substantially parallel to, the plane of tablet 4. By means of electrical leads (not shown), both tablet 4 and stylus base 24 are connected to the computer. Tablet 4 senses the instantaneous position of the stylus, to the effect that any path followed by the handle is shown up as a moving cursor or a continuous line at a scale of 1:1 and in real time on monitor screen 6 and can be analyzed by the appropriate software with which the computer is equipped. Resolution of tablet 4 is of the order of magnitude of 0.05 mm and time resolution is 1 msec.

The quantification of PD in the system according to the invention is based on a combination of two elements: the assessment of control of movement direction, through measurement of vector error in tracing tasks, and the assessment of control of movement speed, through measurement of timeouts in tracking tasks. The combination of these two measurements distinguishes Parkinsonian patients from other subjects in a highly reliable manner that, so far, was unattainable.

The following explains the test procedure according to the invention:

The subject is seated in front of the device, grips handle 22 and, in one set of tests, has to carry out two tasks, each of which is performed first by one hand and then by the other. These tasks are:

a) tracking a target that moves on the monitor screen along a visible path and at controlled speed;

b) tracing a model path in the form of a geometric figure shown on the monitor, in the subject's own time.

During performance of these tasks, the handle 22 and the subject's hand are concealed from the subject's view by the top plate 8, which projects beyond base plate 2 in a direction towards the subject. The tests are thus of the "open loop" type.

The geometries used in a particular set of tests included a circle, a sinusoidal curve and a square.

A further feature of the tracking tasks resides in the fact that whenever the subject's hand (via handle and stylus) moves away from the target beyond a predetermined distance, the target stops and waits for the subject's hand to return to it. This permits the task to be of considerable difficulty, while still allowing every subject to complete it without incurring accumulative errors.

The digitizer and computer software are used to generate the model path, the moving target upon a path, to monitor hand movement, indicating hand location relative to the prescribed path on the monitor, and freezing target movement when the subject strays from the target border, as indicated above.

The data recorded in each test consists of the handle's X, Y, T (=time) coordinates, as sampled at a rate of 100/sec throughout the test. The recorded data is subjected to off-line analysis that generates several parameters of performance, as listed below:

1. Total time of test execution (TT).
2. Vectoral error (VE). This parameter reflects the average magnitude of the movement-vector component that points in a direction perpendicular to that of the model path, given as percentage of the total movement-vector at each sampling point.
3. Cumulative movement time, in which the VE is greater than 50% (T50), i.e., the cumulative time during which movement proceeds away from, or towards, the model path rather than in parallel to it.
4. Mean velocity of the hand (V) in each test.
5. The number of events in which tracking is interrupted (N-outs).

The thus-determined parameters are then compared with values obtained from past experience, to determine the likelihood of the subject to suffer from PD.

Figure 2:
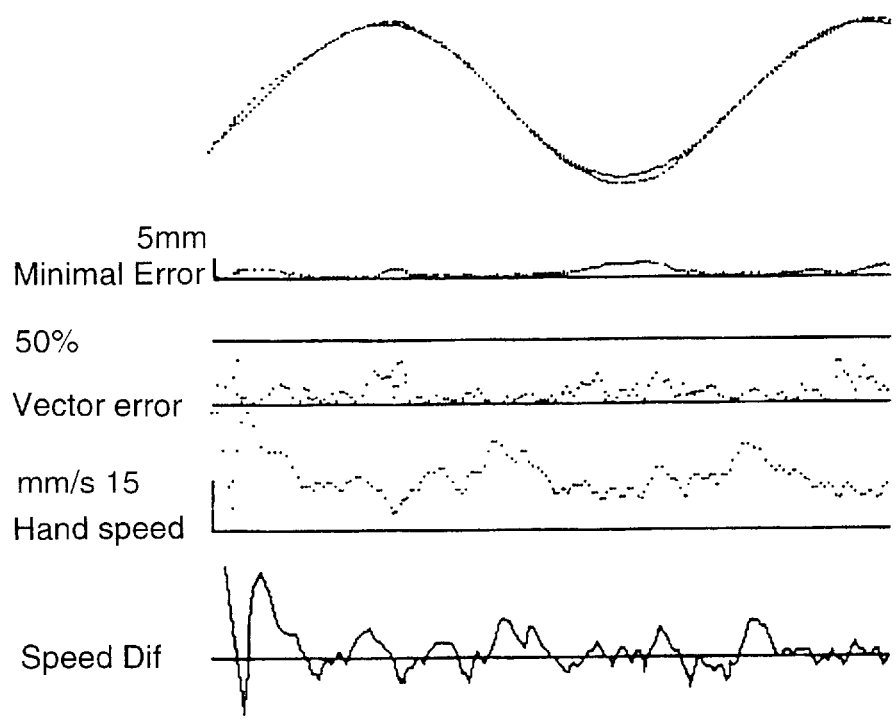

FIG. 2 is an example of data acquired from a test with a non-PD control subject following a sinusoidal path. Analysis yielded the following parameters, some of which are in addition to the above parameters, such as minimal error (mm), mean value of minimal error, and speed difference between target and hand.

Figure 3:
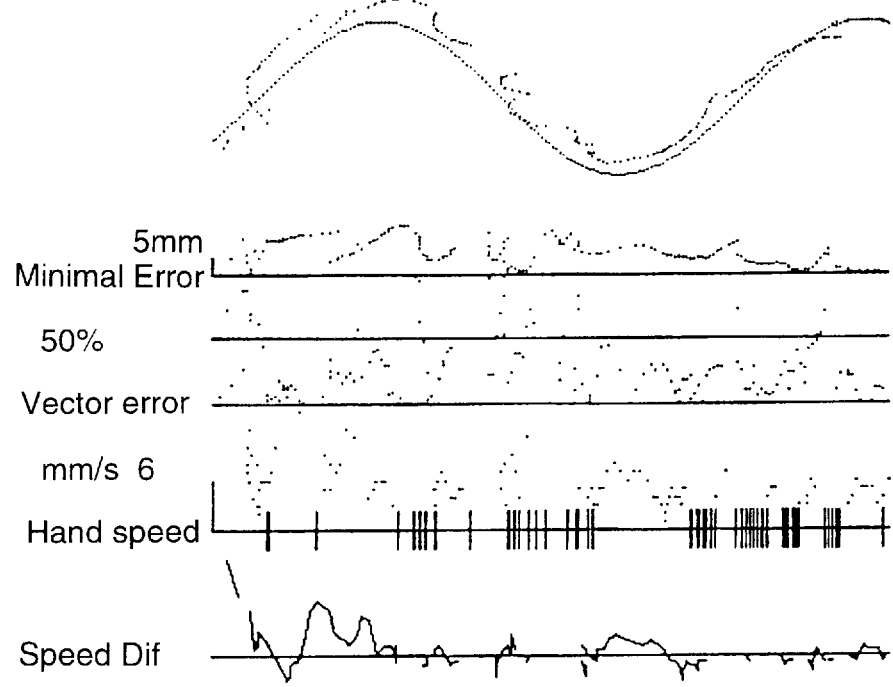

FIG. 3 is a similar collection of data, but this time from a test with a PD subject. The small vertical bars along the base of the hand speed curve denote tracking points where an interruption occurred (N-outs).

The totality of the parameters yielded facilitates a fairly unambiguous identification of PD-afflicted subjects, as compared to subjects suffering from non-PD motor impairments.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A system for detection and quantification of Parkinson's disease, comprising:

a substantially planar digitizer tablet fixedly mounted on a base plate and capable of translating graphic information into digital information displayable, via computer means, as graphic information on a monitor screen viewable by the subject to be tested;

a handle to be gripped and steered by said subject, said handle being fixedly attached to, and supported by, guide means providing said handle with two degrees of freedom in translation in a plane above, and substantially parallel to, the plane of said digitizer tablet;

means for concealing said handle and the subject's hand gripping it from the subject's eyes, said concealing means being a top plate located above said base plate, projecting beyond said base plate in a direction towards said subject to a sufficient degree to conceal said handle in its positions above said digitizer tablet;

a stylus moving together with said handle and adapted to produce signals sensible by said digitizer tablet; and means for producing on said monitor screen a model path of a predetermined shape and size, as well as a target to be tracked by said subject, said target moving at a predetermined speed along said model path;

whereby the quantification of Parkinson's disease for said subject is effected by assessing the direction and speed of the subject's response to said target.

2. The system as claimed in claim 1, wherein said top plate also serves as base plate for said monitor screen.

3. The system as claimed in claim 1, wherein said guide and supporting means is a mechanical linkage system comprising at least two bars articulated to one another, the free end of one of said bars being pivotable mounted on said base plate, and the free end of the other of said bars being attached to said handle.

4. The system as claimed in claim 1, wherein said computer means is adapted to stop said moving target whenever said subject strays by a predetermined distance from said target to be tracked.

5. The system as claimed in claim 1, wherein said stylus is accommodated inside said handle.

6. A method for detection and quantification of Parkinson's disease, comprising the steps of:

providing a substantially planar digitizer tablet fixedly mounted on a base plate and capable of translating graphic information into digital information displayable, via computer means, as graphic information on a monitor screen viewable by the subject to be tested; a handle to be gripped and steered by the subject, said handle being fixedly attached to, and supported by, guide means providing said handle with two degrees of freedom in translation in a plane above, and substantially parallel to, the plane of said digitizer tablet; means for concealing said handle and the subject's hand gripping it from the subject's eyes, said concealing means being a top plate in a direction towards the subject to a sufficient degree to conceal said handle in its position above said digitizer tablet; a stylus moving together with said handle and adapted to produce signals sensible by said digitizer table, and means to produce on said monitor screen a model path of a predetermined shape and size, as well as a target moving at a predetermined speed along said model path;

having the subject grip said handle and track a target displayed on said monitor screen, which target moves at a controlled speed along a visible path;

having the subject grip said handle and trace a model path displayed on said monitor in said subject's own time;

determining the number of times said moving target was lost during the tracking thereof;

determining the mean vectorial error occurring during the tracing of said model path;

determining the cumulative movement time with a vectorial error of a preset magnitude, and comparing the results of said determinations with a set of available values, to determine the likelihood of said subject to suffer from Parkinson's disease.

7. The method as claimed in claim 6, comprising the further step of determining the minimal error.

8. The method as claimed in claim 6, comprising the further step of determining the difference in speed between said target and the hand of said subject.

9. The method as claimed in claim 6, comprising the further step of determining the speed of the subject's hand.

10. The method as claimed in claim 6, comprising the further step of causing said moving target to stop whenever said subject, upon tracking said moving target, strays from said target by a predetermined distance.

* * * * *